US006926666B2

(12) United States Patent
Magee (10) Patent No.: US 6,926,666 B2
(45) Date of Patent: Aug. 9, 2005

(54) PENILE TENSION SYSTEM, DEVICE, KIT, AND METHODS OF USING SAME

(75) Inventor: John F. Magee, Beech Island, SC (US)

(73) Assignee: Augusta Medical Systems, Inc., Augusta, GA (US)

( * ) Notice: Subject to any disclaimer, the term of this patent is extended or adjusted under 35 U.S.C. 154(b) by 0 days.

(21) Appl. No.: 10/752,241

(22) Filed: Jan. 6, 2004

(65) Prior Publication Data

US 2005/0101835 A1 May 12, 2005

Related U.S. Application Data (60) Provisional application No. 60/518,807, filed on Nov. 10, 2003.

(51) Int. Cl.[7] ............................................... A61F 5/00
(52) U.S. Cl. ....................................................... 600/38
(58) Field of Search ..................... 600/38–41

(56) References Cited

U.S. PATENT DOCUMENTS

| | | | | |
|---|---|---|---|---|
| 3,759,253 A | * | 9/1973 | Cray | ........................... 600/41 |
| 4,378,008 A | | 3/1983 | Osbon, Sr. | |
| 4,539,980 A | | 9/1985 | Chaney | |
| 5,306,227 A | | 4/1994 | Osbon et al. | |
| 5,460,594 A | * | 10/1995 | Walling | ........................ 600/38 |
| 5,873,813 A | | 2/1999 | Weiss | |
| 6,039,750 A | * | 3/2000 | Kubalak et al. | ............ 606/201 |
| 6,306,080 B1 | | 10/2001 | Mitchell et al. | |

* cited by examiner

Primary Examiner—John P Lacyk
(74) Attorney, Agent, or Firm—Bracewell & Giuliani LLP (57) ABSTRACT

A penile tensioning system, device, kit, and methods of using same are provided. The penile tensioning device includes a constriction body region of bendable and stretchable material having outer surface peripheries and inner surface peripheries substantially surrounding a medial aperture. The inner surface peripheries are adapted to substantially surround and abuttingly contact outer surface peripheries of a proximal portion of a penis for substantially evenly applying constriction pressure around the circumference of the penis when positioned thereon. The penile tensioning device also includes a pair of the tension positioning and release grips connected to the outer peripheries of the constriction body region, each having a pair of separate and spaced apart finger apertures and positioned substantially opposite each other to impart a stretching force to the constriction body region to increase the inner diameter of the medial aperture to allow positioning and removal of the device from the penis of a user. The system includes the device and a vacuum device to use in the positioning of the device. The kit preferably includes at least one device and a vacuum device.

42 Claims, 7 Drawing Sheets

PENILE TENSION SYSTEM, DEVICE, KIT, AND METHODS OF USING SAME

RELATED APPLICATIONS

This application is related to provisional application Ser. No. 60/518,807 titled "Penile Tensioning System, Apparatus, Kit, and Methods of Using Same, filed on Nov. 10, 2003.

BACKGROUND OF THE INVENTION

1. Field of the Invention

The present invention relates to the medical therapeutic industry and, more particularly, to the field of treatments for male impotence.

2. Description of the Related Art

The male penis includes a pair of corpora cavernosa located laterally within the penis, a pair of penile arteries situated deep within their respective corpora cavernosa, dorsal penal veins and a neurovascular bundle located along an upper proportion of the penis, a corpus spongiosum located along a lower portion of the penis, a urethra located within the corpus spongiosum, and stretchable skin surrounding thereabout. Generally, in the male penis, an erection is produced when arterial blood flows to the erectile tissues of the penis with the veinal return flow of blood to the body restricted so that the erectile tissues become filled or engorged with blood. The restriction is normally performed by sphincter muscles which function in response to sexual arousal. Some men have various problems, e.g., advancing age, physiological or psychological problems, or premature relaxation prior to completion of coitus. This often leaves these men unsatisfied with the sex act process.

Vacuum erection therapy is recognized as a potential remedy, preferable to many other treatments of erection dysfunction such as injections, venous and arterial surgery, or implantation of a penile prosthesis. It provides a firm erection in the shortest time, without need of sexual arousal and can be faster than pills. Vacuum constriction devices include a vacuum chamber with an open end serving as a passage for the penis and a closed end connected to a vacuum pump. To achieve an erection the penis is inserted into the open end of the vacuum chamber, which is pressed to abdomen to form an airtight seal. A vacuum is then generated in the chamber with the manually or electrically operated pump. The vacuum inside the chamber causes blood flow into the penis which thereby produces an erection. The vacuum, however, must be removed for coitus, and thus, the erection can be lost.

By the recognition that penile arteries are located primarily in the deep interior of the male penis, and the return veins are located in a sub-dermal region along the surface of the organ, it has been known to secure a band of material around the base of the penis closely adjacent a user's body to restrict the return veinal blood flow. This assists in maintaining an erection while the arterial flow remains substantially unimpeded, i.e., the arteries are deep within the organ and protected from pressure by the erectile tissue.

Over the years, various types and configurations of bands for assisting in this restriction of the return veinal blood flow have been developed. Though there are many designs, the most popular are devices that encircle the penis. Some of these bands have been developed with a readily detachable fastener which allows the band to be positioned from a substantially open-band configuration to encircle the penis and fasten to a closed configuration. This type of band, however, can often be readily detached by loosening the fastener and is generally not capable of being stretched much in the closed position without the band or fastener breaking or the fastener detaching. The lack of stretching capabilities makes the band difficult, if not impossible, to use with a ring or band loading device which assists in positioning the band over the distal end and onto a proximal portion of a penis. Additionally, these types of bands require extended visualization and significant finger dexterity in order to properly fasten such devices.

Other of these bands, do not provide a fastener, but instead allow a closed band to be stretched for positioning over a distal end of the penis and moved to the proximal end, i.e., the base of the penis for release into a penile constricted position or can be positioned using a ring or band loading device. For example, U.S. Pat. No. 4,378,008 by Osbon, Sr. titled "Erection Aid Device" describes a constricted device which encircles the penis. Also described is a band stretching and positioning tool, typically referred to as a ring loader, developed to aid in the positioning process of these bands.

Under similar principles, the vacuum device can have the constriction rings or bands placed on the vacuum chamber close to its open end and can be used to aid in the positioning process of these bands. To sustain the erection, the constriction ring or band can be preinstalled on the open proximal end of the device and can be forced to slip off onto the root of the penis. Being placed on the root of the penis, the constriction ring or band inhibits the blood flow from the penis and thus sustains the erection. After this, the vacuum is released, and the chamber is removed from the erect penis.

A problem with these types of bands, however, is that they typically require an excessive amount of lubricant to position them properly over the penis shaft, and once positioned on an erect penis, they are not easily removed, replaced, or repositioned, due to the looseness and flexibility of the stretchable skin surrounding the penis. Additionally, once the user is finished with the band and the band is in a tight constricted position, the band can be difficult to remove back over the distal end of the penis, especially over an enlarged organ and over the head (glands penis) of the penis. Also, a band left on a penis in the tight constricted position can cause pain, bruising or other problems with the penis.

Some more recent devices include elastic loops for adjusting the position of the device in an attempt to enhance comfort and improve performance of the device. For example, U.S. Pat. No. 4,539,980, by Chaney titled "Male Organ Conditioner," describes an apparatus including a central elastic ring having a durometer number of about 55 and a pair of lateral extending integral semicircular shaped elastic loops. The central ring includes an opening which, when expended, can be passed over the penis down to its root. The relatively small ends of each of the loops are equiangularly spaced around the ring such that when the loops are stretched laterally the central ring will expand orthogonally into a square shape for positioning over the penis. The ring can be installed either manually or with a ring loader. In order to manually install the central elastic ring, the user positions two or three fingers in each loop and spreads the fingers to stretch the loops and spreads the hands from each other to deform the central elastic ring along two perpendicular planes. After positioning the central elastic ring, the user releases the ring loops to allow the ring to contract and inhibit ingress and egress of blood to and from the penis. The user then performs a forward massaging action from under the scrotum to force blood through the pre-positioned central ring to obtain to desired size and rigidity. The apparatus optionally features a second pair of loops also integral with the central elastic ring and connected coincident with the first pair of loops, the upper of the second pair of loops to provide clitoris stimulation.

Also for example, U.S. Pat. No. 5,306,227, by Osbon et al. titled "Apparatus for Augmenting Male Potency" also describes a cincture band of elastic material which also includes a protruding region positioned to provide a recess to receive the urethra of a user's male sex organ. The pair of loops are centered about 90 ninety degrees from the center of the protruding region, opposite each other, to thereby provide a user handles to manipulate the cincture band to position the protruding region over the urethra. The handles can also be used to manually expand their ring for placement over a flaccid male sex organ. The cincture band and loops can be circular in shape to prevent the introduction of sharp edges around the male sex organ and to facilitate manufacturer of the apparatus. The diameter of the loops is smaller than the cincture band in order to allow positioning of the apparatus within the open proximal end of a vacuum chamber. The apparatus can also include a pair of radially inward protruding regions within the inner diameter of the cincture band having cylindrical pressure point members consisting of an inelastic material inserted therein to provide added pressure to restrict bloodflow from the subcutaneous lateral veins without applying direct force to the center of the dorsal region. The apparatus can be inserted with use of a first vacuum device. Thereafter, the loops of the apparatus are bent forward and a second vacuum device is positioned over the apparatus and the male sex organ to provide additional erection or firmness. The first vacuum device includes a body having a smaller distal end which, in conjunction with use of a lubricant such as petroleum jelly, is utilized to help expand the apparatus for placement over the male sex organ. The first vacuum device also includes a proximal organ adapter having a larger outer diameter than the main body of the first vacuum device to allow further expansion of the apparatus for placement over the male sex organ.

Though somewhat successful in providing the user the ability to make minor adjustments to the position of the apparatus or device, these devices, however, have proved to be insufficient both in providing a user the ability to stretch the functional body of the device over an insertion device and in providing a user the ability to stretch the functional body of the device over the glands penis of the male sex organ when the male sex organ is not flaccid. During manual extension, the point-like attachment of and position of the loops or handles generally result in a user causing a nonsymmetrical deformation of the inner diameter of the apparatus or device, whereby the inner diameter is significantly increased or stretched along a plane between the center of the loops (horizontal plane) and the inner diameter is decreased in a plane perpendicular to said parallel plane (vertical plane). This can cause a tightening along the vertical plane which tends to compress the dorsal vein and neurovascular bundle and the urethra, which can result in added difficulty in removing the apparatus or device. Additional force is often required to overcome this reduction in inner diameter. Also, the nonsymmetric stretching increases the likelihood of pinching or rubbing of the skin during the stretching or contraction of the ring. Additionally, the attachment points tend to suffer structural fatigue.

Other recent devices also include handles to allow for both positioning and either independent insertion or removal of the device from the penis. For example, U.S. Pat. No. 5,873,813 by Weiss titled "Method and Apparatus for Producing and Maintaining a Penile Erection" describes an apparatus having a resilient ring member defining an inner opening through which a penis is inserted. The resilient ring member is surrounded by a cloth mesh substrate material encapsulated in an elastomer, such as medical grade silicon, which is adapted to contact the shaft of the penis. The apparatus includes a pair of spaced apart handles extending outwardly from the resilient ring member to allow the user to adjust the cross-sectional area of the inner opening housing the penis. The resilient ring is opened with the handles and inserted over a flaccid penis. The ring is then slide toward the distal end of the penis away from the shaft to capture blood released, reposition to the shaft, and again slid until the penis is of a sufficient constriction. The resilient ring is then placed at the base of the penis in the closed position to maintain the erection.

Because the handles can easily slide from the fingers of the hands of the user, these types or devices, however, have proved somewhat difficult to manipulate. These types of devices also do not lend themselves to use with a vacuum device but are instead intended to replace such device. Also, these types of devices can be uncomfortable to the user. Besides generally being designed so that one size fits all, by their nature the parts of the structure surrounding the penis and the stems for the handles must be of a resilient material such as a resilient wire.

Applicant, therefore, has recognized a need for a penile tensioning device which which allows the user to provide substantially even pressure on the sides of the penile tensioning device to radially expand a central or medial aperture of a elastic penile tensioning body with minimal geometric deformation of the shape of the aperture, and which provides easy and comfortable removal over an erect glands penis after intercourse. Also, Applicant has recognized a need to provide substantially even contraction pressure around the circumference of any erect penis. Also Applicant has recognized the need for such a non-disposable device manufactured with an ergonomic geometrical shape to provide a natural, comfortable feeling to the user and partner during use.

SUMMARY OF THE INVENTION

With the foregoing in mind, the present invention advantageously provides a penile tension device which can be both easily stretched for inserting over a male penis and yet can be readily repositioned or removed over the enlarged organ and over the glands penis. The present invention also advantageously provides a penile tensioning device, penile tensioning system, penile tensioning kit, and associated methods of use which allow the user to easily position the penile tensioning device over an erect penis and allow for ease of removal from the base of the penis. The present invention additionally advantageously provides a penile tensioning device which can readily be molded in large quantities and yet still have the above described advantages. The present invention further advantageously provides a penile tensioning device and associated methods which can easily be used with vacuum assist erection devices, band or ring loaders, and other penile erection devices from various manufacturers and yet still have the above described advantages.

More particularly, the present invention provides a penile tensioning device which includes a body region of bendable and stretchable material formed in a closed band shape defining a constriction body region having outer constriction body peripheries and inner constriction body peripheries which substantially surround a medial aperture. The inner construction body peripheries are adapted to substantially surround and abuttingly contact outer penile surface peripheries of a proximal portion of a penis of a user for substantially evenly applying constriction pressure around the circumference of the penis when positioned thereon. The medial aperture includes a longitudinal medial aperture axis, a longitudinal medial aperture length, and a preselected inner medial aperture diameter.

The penile tensioning device also includes a plurality of tension positioning and release grips formed of a bendable material connected to the outer constriction body peripheries of the constriction body region. Each of the grips can have a pair of separate and spaced apart finger apertures adapted to receive a corresponding pair of fingers of a user. A first of the plurality of tension positioning and release grips is generally positioned substantially opposite a second of the plurality of tension positioning and release grips for the user to impart a radial outwardly directed stretching force to the constriction body region to increase the predetermined inner center aperture diameter. This is accomplished to allow positioning of the penile tensioning device in abutting contact with the outer surface peripheries of the proximal portion of the penis to allow constriction of bloodflow to the penis, and to allow removal of the penile tensioning device from abutting contact with the outer surface peripheries of the proximal portion of the penis to allow for passage of the penile tensioning device over a glands penis of an erect penis. The penile tensioning device can also include a plurality of tensioning ribs positioned uniformly and axially spaced apart along the inner constriction body peripheries of the constriction body region and extending within the medial aperture, extending parallel to the longitudinal medial aperture axis, and can extend substantially the longitudinal medial aperture length to provide even constriction pressure around the outer peripheries of the proximal portion of the erect penis.

Advantageously, an embodiment of the present invention also includes a penile tensioning system for forming and maintaining an erect penis. The system comprises a penile tensioning device, such as that described above, including a body region of bendable and stretchable material formed in a closed band shape defining a constriction body region having outer constriction body peripheries and inner constriction body peripheries which substantially surround a medial aperture and a plurality of tension positioning and release grips formed of a bendable material connected to the outer constriction body peripheries of the constriction body region. The system also comprises a vacuum device including an elongated vacuum chamber having a proximal end and a distal end, the proximal end adapted to receive the penile tensioning device thereon and adapted to receive the penis therein. The vacuum chamber is adapted to be brought into contact with a user adjacent the proximal end of the penis against a body of the user in order to position the penile tensioning device in abutting contact with the outer surface peripheries of the proximal portion of the erect penis. The vacuum device further includes a pressure pump adapted to be connected to the distal end of the vacuum chamber for creating a vacuum pressure inside the vacuum chamber. The distal end of the vacuum chamber is adapted to be positioned in fluid communication with the pressure pump whereby a pressure is created by the pressure pump inside the vacuum chamber and is exerted upon the penis received therein to form the erect penis.

Advantageously, an embodiment of the present invention also includes a penile tensioning kit for forming and maintaining an erect penis comprising a container, at least one but preferably a plurality of differently sized penile tensioning devices, described above, positioned within the container, a practice penile tensioning device similar to the penile tensioning device but having a constriction body region of increased elasticity and softness for performing practice penile tensioning and removal positioned in the container, and a vacuum device also positioned in the container.

Advantageously, an embodiment of the present invention also provides methods of using a penile tensioning device. A method of using a penile tensioning device preferably includes stretching a constriction body region of a penile tension device by a plurality of fingers of a user positioned in a pair of positioning and release grips associated with the penile tension device so that an opposing force is applied to major lengthwise extents of opposing sides of the constriction body region to thereby expand a medial aperture of the constriction body region sufficiently to position the stretched constriction body region over a distal end of a penis of the user and toward a proximal portion of the penis.

An embodiment of the present invention also advantageously provides alternative methods of using a penile tensioning device. A method includes stretching a constriction body region of a penile tension device by a plurality of fingers of a user positioned in a pair of positioning and release grips associated with the penile tension device so that an opposing force is applied to the major lengthwise extents of the opposing sides of the constriction body region to thereby expand a medial aperture of the constriction body region sufficiently to position the stretched constriction body region over a proximal end of a vacuum device for placement over a penis of the user. The method also includes repositioning the device off the proximal end of the vacuum device and to a proximal portion of the erect penis of the user, thereby releasing the stretch of the constriction body region so that inner constriction body peripheries of the constriction body region abuttingly contact with and provide substantially uniform constriction pressure around outer penile surface peripheries of the proximal portion of the penis.

Advantageously, embodiments of the present invention provide a nondisposable penile tensioning device that can be easily repositioned after installation. Embodiments of the present invention also provide for the application of uniform pressure on the sides of the penile tensioning device to radially expand a medial aperture. The application of such force can provide for minimal geometric deformation of the shape of the medial aperture which provides for easy and comfortable removal over an erect glands penis. Advantageously, embodiments of the present invention also provide a penile tensioning device having an ergonomic geometrical shape to provide a natural, comfortable feeling to the user and partner during use.

BRIEF DESCRIPTION OF THE DRAWINGS

So that the manner in which the features and advantages of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and are therefore not to be considered limiting of the invention's scope as it may include other effective embodiments as well.

DETAILED DESCRIPTION

The present invention will now be described more fully hereinafter with reference to the accompanying drawings, which illustrate embodiments of the invention. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout. Prime notation, if used, indicates similar elements in alternative embodiments.

Figure 2:
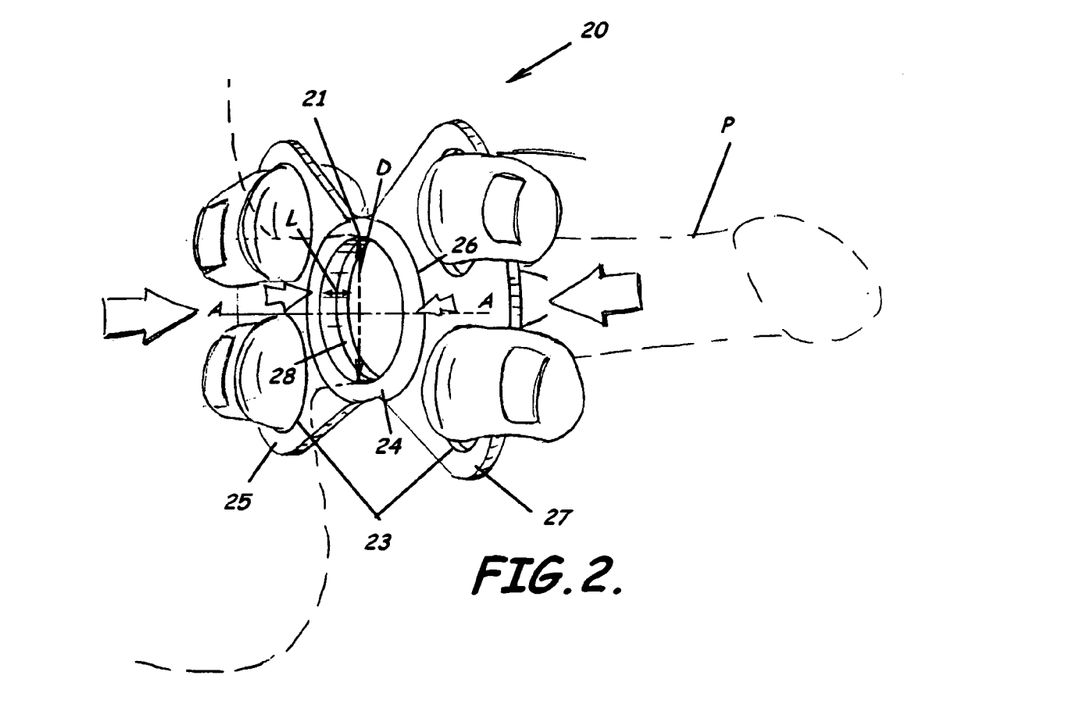
FIG. 2 is a perspective environmental view of the penile tensioning device of FIG. 1 positioned at the base or proximal end portion of a male penis, according to an embodiment of the present invention.
Figure 3:
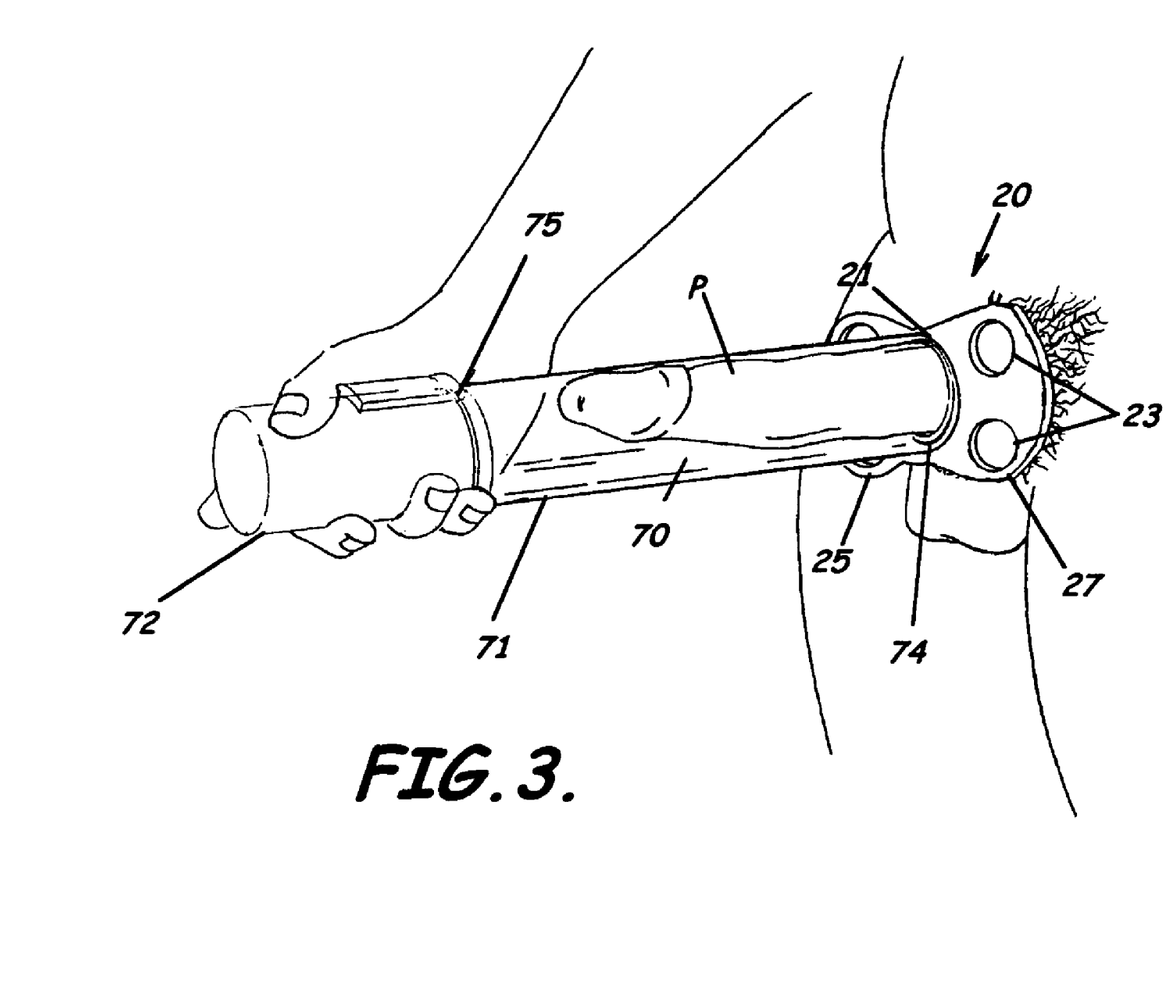
FIG. 3 is a perspective environmental view of the penile tensioning device of FIG. 1 positioned at the base or proximal end portion of a vacuum device, according to an embodiment of the present invention.
Figure 4:
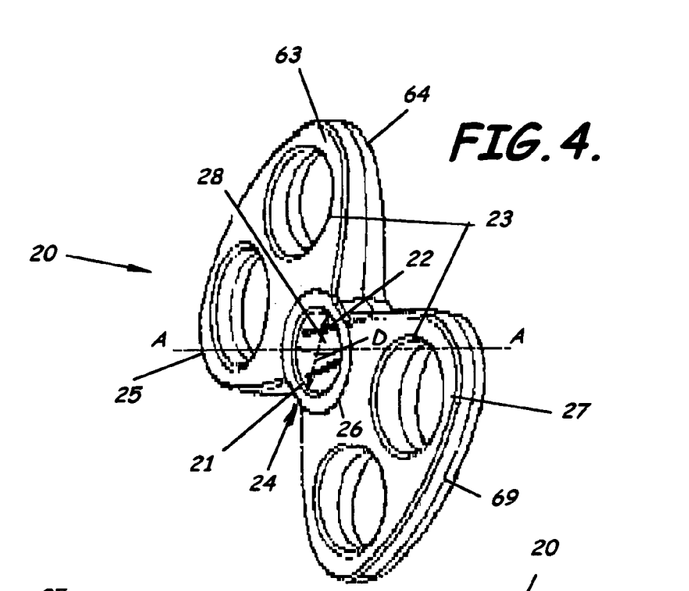
FIG. 4 is a perspective view of the penile tensioning device of FIG. 1, according to a first embodiment of the present invention.
Figure 5:
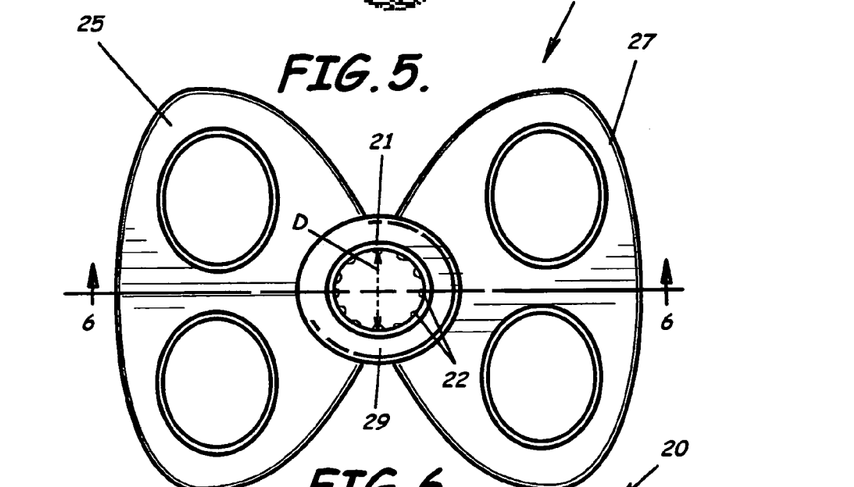
FIG. 5 is an enlarged front elevational view of the penile tensioning device of FIG. 4, according to a first embodiment of the present invention.

FIGS. 1–12 illustrate 5 different embodiments of a durable penile tensioning device 20 according to the present invention. As shown in FIGS. 4–5 the penile tensioning device 20 preferably includes a body region of bendable and stretchable material formed in a closed band shape defining a constriction body region 24 having outer constriction body peripheries 26 and inner constriction body peripheries 28 substantially surrounding a medial aperture 21. The medial aperture 21 has a proximal end 61 and a distal end 62 and includes a longitudinal axis A, a longitudinal length L, and a preselected inner diameter D. The inner constriction body peripheries 28 of the constriction body region 24 are adapted to substantially surround and abuttingly contact outer surface peripheries of a proximal portion of a penis P (see FIG. 2) for substantially evenly applying constriction pressure around the circumference of the penis P when positioned thereon.

Figure 6:
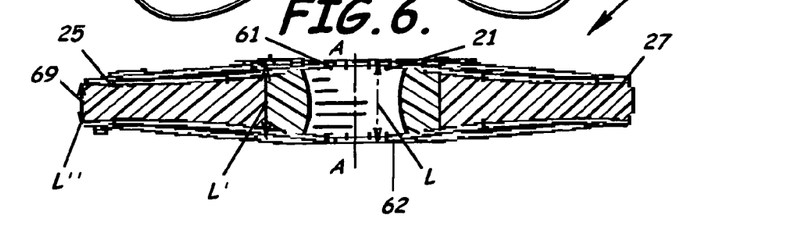
FIG. 6 is an enlarged side elevational view of the penile tensioning device of FIG. 4, according to a first embodiment of the present invention.

As perhaps best shown in FIG. 6, the inner constriction body peripheries 28 which define the outer periphery of the medial aperture 21 are preferably arcuate along the length L extending parallel to longitudinal axis A of the medial aperture 21 and extending between the proximal and distal ends 61, 62, to provide greater tensioning at a midpoint of the length L of the medial aperture 21 than at the proximal or distal ends 61, 62. This arcuate shape reduces the risk of bruising of the skin related to an imprinting effect resulting from the transition between those outer surface peripheries of the proximal portion of the penis P subjected to constriction pressure and those adjacent the penal tensioning device not subjected to constriction pressure, when the penile tensioning device 26 is so positioned. Additionally, as shown in FIG. 5, a predefined portion of material 29 of the constriction body region 24 is adapted to be positioned adjacent the urethra during positioning at the proximal portion of the penis P with use of tensioning and removal grips 25, 27 (described later). Preferably the predefined portion of material 29 is softer, having a lower durometer number, than other portions of the material of the constriction body region 24.

As shown in FIGS. 4–5, the penile tensioning device 20 can also include a plurality of tensioning ribs 22 connected to and preferably positioned uniformly and axially spaced apart along the inner constriction body peripheries 28 of the constriction body region 24 and extend inwardly into the medial aperture 21. The length of the tensioning ribs 22 preferably extend parallel to the longitudinal axis A of the medial aperture 21 and preferably extend substantially the longitudinal length L of the medial aperture 21. The shape and positioning of the tensioning ribs 22 advantageously can enhance the evenness or uniformity of the constriction pressure provided by the medial aperture 21 around the outer peripheries of the penis P, can reduce the likelihood of pinching or rubbing of the skin of the penis P during positioning or removal of the penile tensioning device 20, can provide for improved circulation of the skin surface while providing sufficient compression to establish and maintain the erect penis P, and can allow for use of a softer material in the construction of the inner constriction body peripheries 28. The tensioning ribs 22 also can be arcuate or tapered along their length to minimize potential penile skin damage between a region of constriction within the constriction body region 24 and regions of non-constriction outside the constriction body region 24 along the proximal and distal ends of the ribs 22. This can be an especially important advantage where the inner constriction body peripheries 28 are not arcuate. The tensioning ribs 22 can alternatively have other configurations. For example, the tensioning ribs 22 can have a longitudinal axis angled acutely with the longitudinal axis A, have a laterally curved or snake-like shape, or have a spiral shape with respect to the inner constriction body peripheries 28.

Advantageously, the penile tensioning device 20 includes preferably a pair of tension positioning and release grips 25, 27, formed of a bendable material joined or connected to major lengthwise extents 65, 67, of the outer peripheries 26 of the constriction body region 24 preferably having an arcuate shape and preferably located substantially parallel to an arc of a circumference of the medial aperture 21. The tension positioning and release grips 25, 27, are preferably formed separately from a harder material having a higher durometer number than that of the constriction body region 24, and are connected to the major lengthwise extents 65, 67, of the outer peripheries 26 with a flexible adhesive or other method as known by those skilled in the art. Alternatively, the tension positioning and release grips 25, 27, can be unitary with the constriction body region 24. The tension positioning and release grips 25, 27, each have preferably at least pair of separate and spaced apart finger apertures 23 adapted to receive at least a corresponding number of fingers F of the user to provide the user the ability to impart the force necessary to position the penile tensioning device 20 on or off the penis P.

Figure 1:
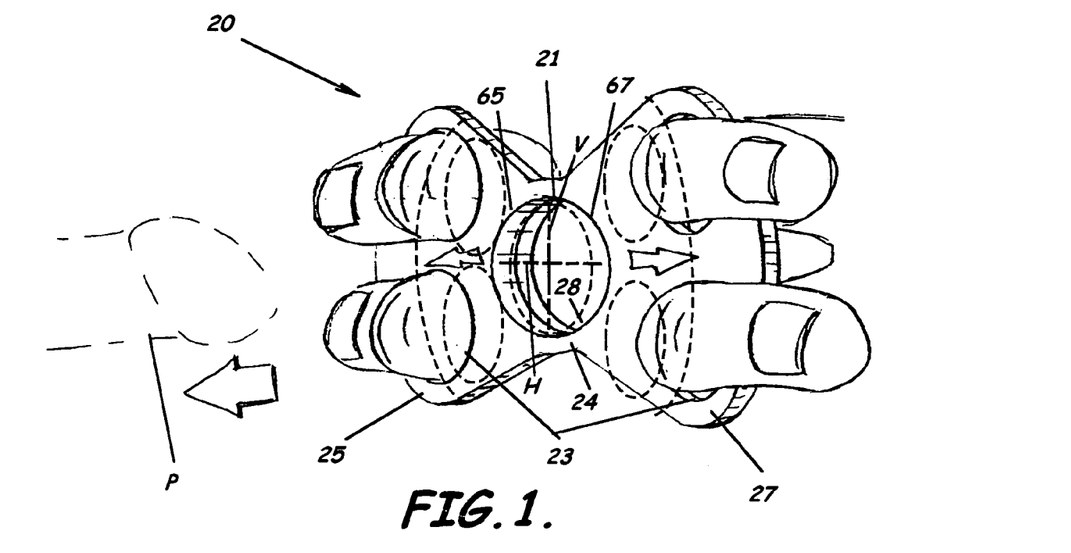
FIG. 1 is a perspective environmental view of a penile tensioning device having a body region of bendable and stretchable material and a pair of tension positioning and release grips, according to an embodiment of the present invention.

As shown in FIG. 1, one of the pair of tension positioning and release grips 25 can be substantially positioned opposite the other of the pair of tension positioning and release grips 27 for imparting an opposing radial outwardly directed stretching force to the constriction body region 24 to increase the inner diameter of the medial aperture 21 to position the penile tensioning device 20 on the penis P of the user. Specifically, the user positions a plurality of fingers F in a pair of finger apertures 23 located on each of the pair of tension positioning and release grips 25, 27, and exerts a radially outwardly directed or opposing stretching force to each of the pair of finger apertures 23 to stretch the inner diameter D of the medial aperture 21. The outwardly directed force applied by the separate pair of fingers F of the user is translated through the tension positioning and release grips 25, 27, to the major lengthwise extents 65, 67, of the outer peripheries 26 of the constriction body region 24 to provide less geometric deformation than would be achieved if the tension positioning and release grips 25, 27, were connected to the outer peripheries 26 of the constriction body region 24 at a single point or pair of points. This construction advantageously helps reduce pinching or rubbing of the skin of the penis P during the positioning or removal of the penile tensioning device 20. As shown in FIG. 2, once sufficiently stretched, the user then positions the penile tensioning device 20 at the base or proximal end of the penis P and releases the opposing force. This is accomplished to allow positioning of the penile tensioning device 20 in abutting contact with the outer surface peripheries of the proximal portion of the penis P to provide constriction of bloodflow to the penis P to help form and maintain an erection in the penis P.

As shown in FIG. 1, once the penile tensioning device 20 is installed to the proximal portion of the penis P of the user, the pair of tension positioning and release grips 25, 27, can again be used to impart an opposing radial outwardly directed stretching force to the outer periphery 26 of the constriction body region 24 to increase the inner diameter D of the medial aperture 21 to allow repositioning of the penile tensioning device 20 or removal of the penile tensioning device 20 from abutting contact with the outer surface peripheries of the proximal portion of an erect penis P after intercourse. The user again positions the plurality of fingers F from each hand through the pair of finger apertures 23 in the tension positioning and release grips 25, 27, and exerts an opposing force to stretch the inner diameter D of the medial aperture 21 sufficiently to allow for passage of the penile tensioning device 20 over a glands penis. The user then extends the penile tensioning device 20 beyond the glands penis and releases pressure on the tension positioning and release grips 25, 27.

As shown in FIGS. 4–6, advantageously, an embodiment of the present invention provides an ergonomic geometrical shape which is both functional and aesthetic. Particularly, the shape of the portion of the tension positioning and release grips 25, 27, adjacent the medial aperture 21 can be such that application of an opposing radial outwardly directed stretching force to the outer periphery 26 of the constriction body region 24 applied to increase the inner width or diameter D of the medial aperture 21 causes application of stretching force such that the inner diameter D of the medial aperture 21 expands along a horizontal axis H without significantly decreasing the inner width or diameter D along a V vertical axis. This helps prevent the application of direct force to the center of the dorsal region of the penis P, the application of which typically results in an increase in the difficulty of removing the device 20, i.e., increasing compressive forces on the dorsal region of penis P tend to maintain or increase the rigidity of the penis P. In the preferred configuration, application of the opposing radial outwardly directed stretching force to the outer periphery 26 of the constriction body region 24 can result in the application of a positive outwardly directed stretching force or even a substantially equal stretching force along the vertical axis V as that of the horizontal axis H. In the preferred configuration, additionally, the shape and rigidity of the tension positioning and release grips 25, 27, are such that the shape of the finger apertures 23 are substantially unaffected by the application of the opposing forces, thus providing the user a stable platform to perform the stretching operation.

As shown in FIG. 6, the penal tensioning device 20 can also be shaped such that the tension positioning and release grips 25, 27, adjacent the medial aperture 21, each have a longitudinal length L' substantially similar to that of length L of the medial aperture 21 of the constriction body region 24 whereby the longitudinal length progressively decreases along the width of the tension positioning and release grips 25, 27, between the outer constriction body peripheries 26 and outer peripheries 69 of the grips 25, 27, to region length L". The shape provides a more natural, comfortable feeling to the user and to the partner of the user during use.

Figures 7, 8:
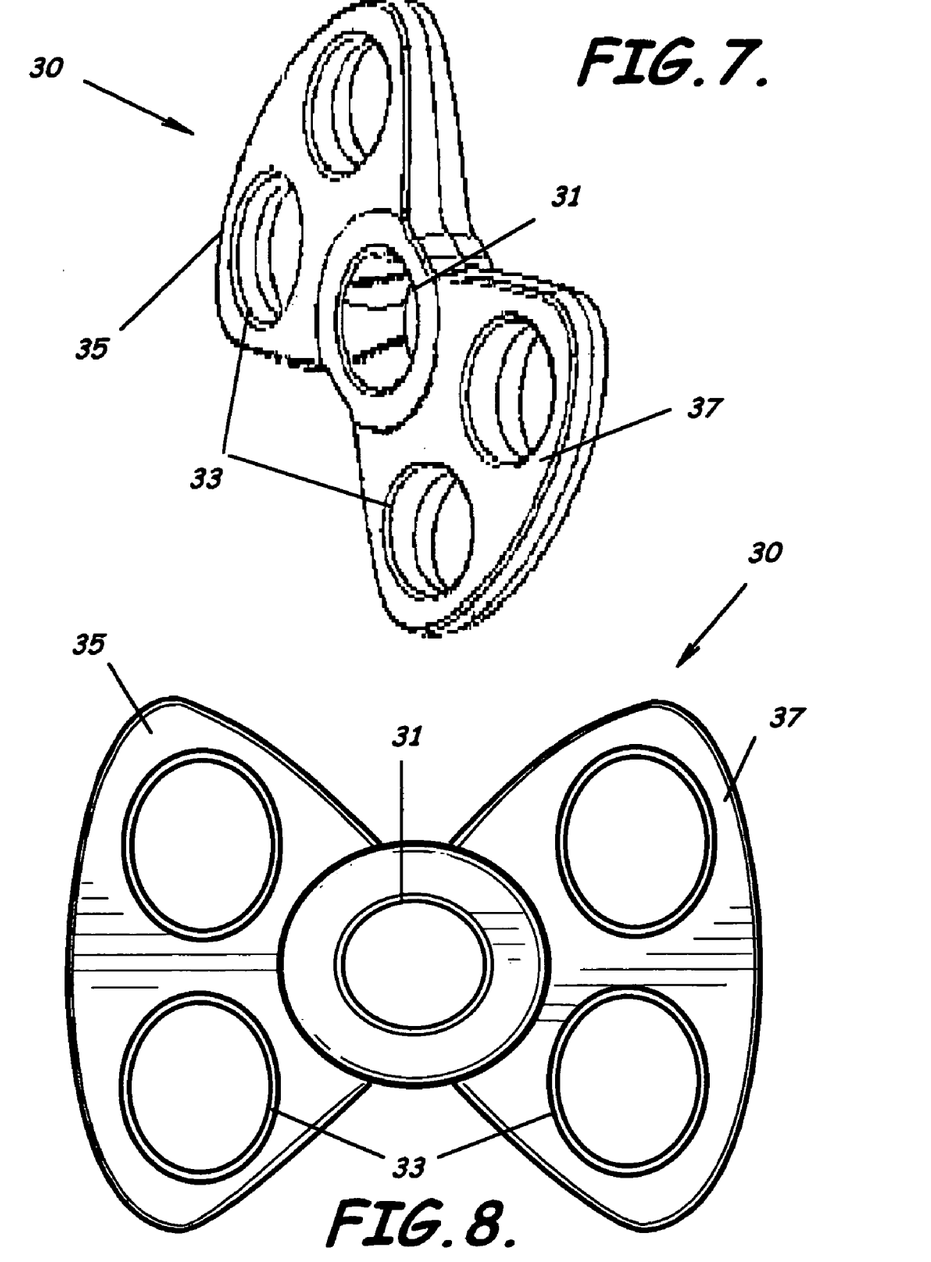
FIG. 7 is a perspective view of a penile tensioning device, according to a second embodiment of the present invention.
FIG. 8 is an enlarged front elevational view of the penile tensioning device of FIG. 7, according to a second embodiment of the present invention.
Figure 9:
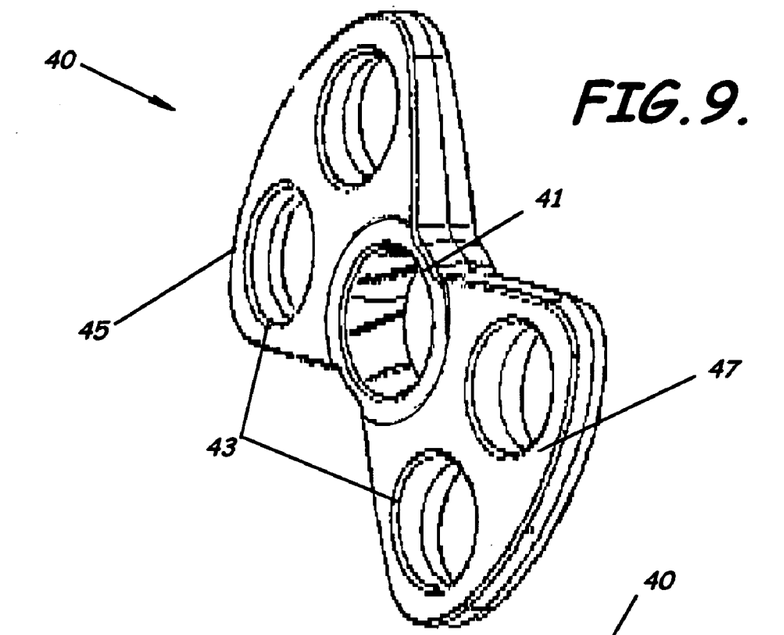
FIG. 9 is a perspective view of a penile tensioning device, according to a third embodiment of the present invention.
Figure 10:
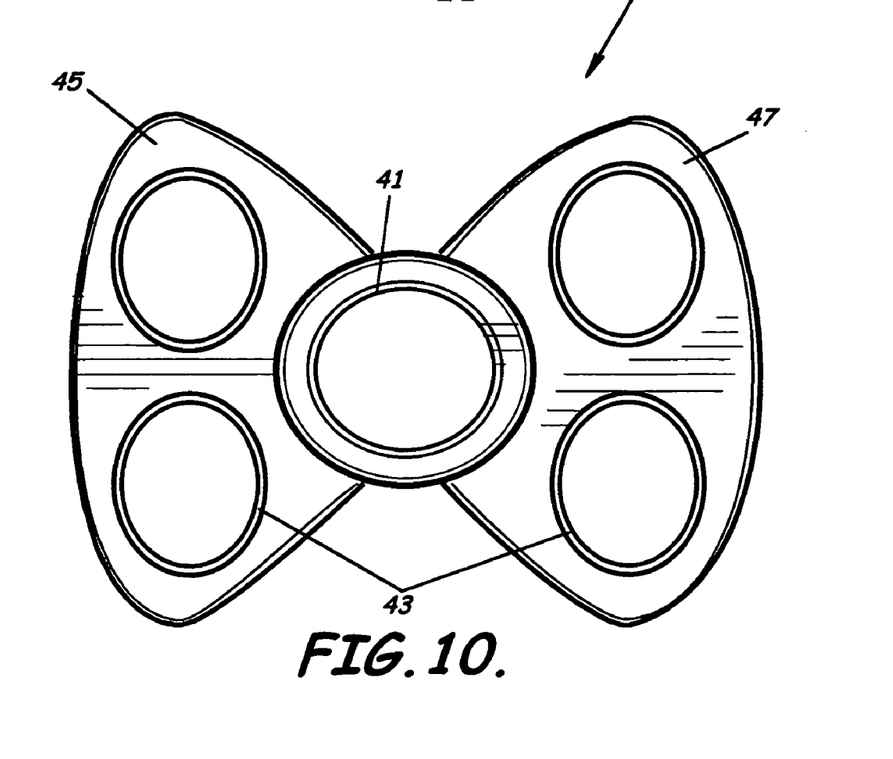
FIG. 10 is an enlarged front elevational view of the penile tensioning device of FIG. 9, according to a third embodiment of the present invention.
Figure 11:
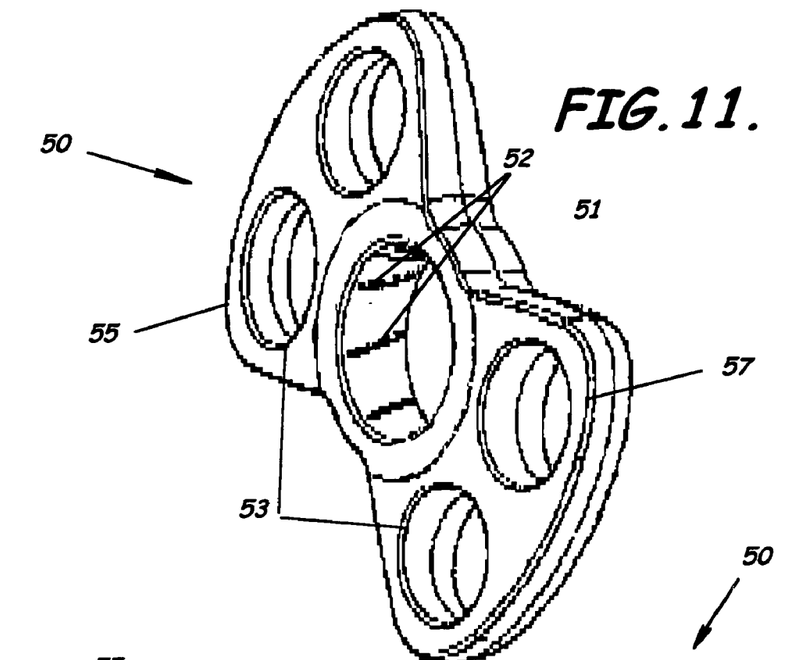
FIG. 11 is a perspective view of a penile tensioning device, according to a fourth embodiment of the present invention.
Figure 12:
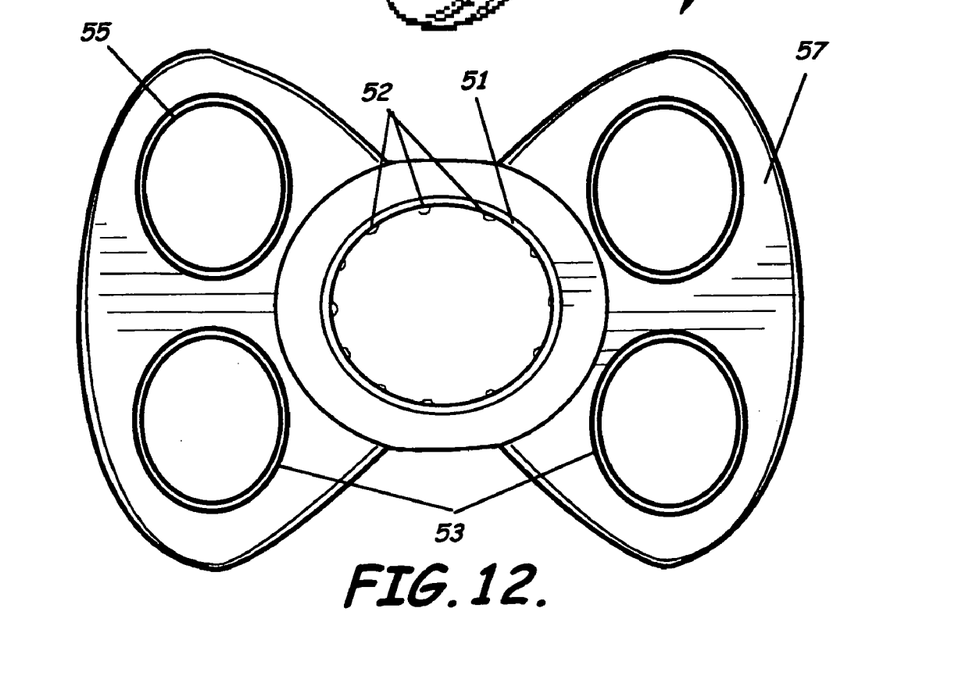
FIG. 12 is an enlarged front elevational view of the penile tensioning device of FIG. 11, according to a fourth embodiment of the present invention.

Advantageously, the penile tensioning device 20 can accommodate an array of various sizes of male sex organs. As shown in FIGS. 4–5, the medial aperture 21 of the constriction body region 24 has a diameter D that is preferably sized relatively small, according to a first embodiment of the present invention. In this embodiment, the finger apertures 23 in each of the tension positioning and release grips 25, 27, are spaced apart sufficiently such that the medial aperture and one of the finger apertures 23 on each of the tension positioning and release grips 25, 27, are approximately in alignment to optimize the ability to stretch the medial aperture 21 through use of the tension positioning and release grips 25, 27. Additionally, the finger apertures 23 of the grips 25, 27, can be larger than the inner diameter of the medial aperture 21. As shown in FIGS. 7–8, a second embodiment of the present invention 30 is similar in design and shape to the first embodiment 20 except that the medial aperture 31 is larger and thus the spacing between the respective finger apertures 33 and over all width of the device 30 can be increased in order to achieve approximate alignment of one of the finger apertures 33 on each of the tension positioning and release grips 35, 37, with the medial aperture 31 and to accommodate expectedly larger fingers. As shown in FIGS. 9–10, a third embodiment of the present invention 40 is similar in design and shape to the second embodiment 30 except that the medial aperture 41 is even larger and thus the spacing between the respective finger apertures 43 and over all width of the device 40 can be increased in order to achieve approximate alignment of one of the finger apertures 43 on each of the tension positioning and release grips 45, 47, with the medial aperture 41. As shown in FIGS. 11–12, a fourth embodiment of the present invention 50 is similar in design and shape to the third embodiment 40 except that the medial aperture 51 is yet even larger and thus the spacing between the respective finger apertures 53 and over all width of the device 50 can again also be increased in order to achieve approximate alignment of one of the finger apertures 53 on each of the tension positioning and release grips 55, 57, with the medial aperture 51.

As shown in FIGS. 4–12, advantageously, the shape of the penile tensioning device 20 according to various embodiments of the present invention allows for efficient manufacturing and assembly. In the preferred methodology, the constriction body region 24 can be molded as a unitary unit and the tension positioning and release grips 25, 27, can be either molded as individual units or each half grip 63, 64 can be molded separately, laminated together to form a pair of grips 25, 27, and then laminated to the constriction body region 24. Alternatively, the penile tensioning device 20 can be molded in separate half sections and laminated together. Each of the distal and proximal faces or halves 63, 64, of the tensioning and release grips 25, 27, along with half of the constriction body region 24 are initially formed in a single mold, and, after formation, the two sides 63, 64, and the two halves of the constriction body region 24 are then laminated together to form the device 20. Alternatively, the constriction body region 24 and grips 25, 27 can be molded separately, laminated together individually, then laminated together as a unit. The penile tensioning device 20 can also, alternatively, be molded merely as one unitary body.

As shown in FIGS. 1–12, advantageously an embodiment of the present invention includes a system for forming and maintaining an erect penis. The system preferably includes a penile tensioning device 20 and a vacuum device 70 adapted to receive a penis P in order to form an erect penis P. The penile tensioning device 20, described in detail above, as a minimum includes a body region of bendable and stretchable material formed in a closed band shape defining a constriction body region 24 having outer constriction body peripheries 26, inner constriction body peripheries 28, and a plurality of tension positioning and release grips 25, 27. The inner constriction body peripheries 28 of the constriction body region 24 substantially surround a medial aperture 21, forming an outer periphery of the medial aperture 21. The medial aperture 21 includes a longitudinal axis A, a longitudinal length L, and a preselected inner width or diameter D. The inner constriction body peripheries 28 of the constriction body region 24 is adapted to substantially surround and abuttingly contact outer surface peripheries of a proximal portion of a penis P for substantially evenly applying constriction pressure around the circumference of a penis P when so positioned thereon. The tension positioning and release grips 25, 27, are preferably formed of a bendable material connected to the outer constriction body peripheries 26 of the constriction body region 24 along major lengthwise extents 65, 67, as described above. Each of the tension positioning and release grips 25, 27, have a pair of separate and spaced apart finger apertures 21 adapted to receive a corresponding plurality of fingers F of the user.

As shown in FIG. 3, the vacuum device 70 includes an elongated vacuum chamber 71 and a pressure pump 72. The elongated vacuum chamber 71 has a proximal 74 and a distal end 75. The outer surface of the proximal end 74 is adapted to receive the penile tensioning device 20. The penile tensioning device 20 is positioned on the outer surface of the proximal end 74 by expanding the medial aperture 21 similar to the manner described above and positioning the device 20 over the proximal end 74 of vacuum chamber 71. The proximal end 74 of the vacuum chamber 71 is adapted to receive the penis P therein and the distal end 75 is adapted to be positioned in fluid communication with the pressure pump 72. Functionally, during operation the proximal end 74 by the vacuum chamber 71 is brought into contact with the user adjacent the proximal end of the penis P while the opposite distal end 75 is generally held away from the body (i.e., torso) of the user. When the pressure pump 72 is operating, a pressure is created inside the chamber 71 and exerted upon the penis P received therein. The pressure pump 72 can be either manual or electric. Soma Blue Response®II, manufactured by Augusta Medical, Inc., Augusta, Ga., provides an example of a vacuum device having a manual pressure pump having a pump handle and actuation arm. Soma Blue Touch®II provides an example of an electric pressure pump which conceptually functions the same as the manual pump except instead of a pump handle and actuation arm, the pump includes an electric motor and a button.

Regardless of the type of pressure pump used, once the pressure pump 72 is actuated, air is drawn out of the vacuum chamber 71 causing negative pressure (i.e., vacuum) to be created inside the chamber 71. This negative pressure causes blood to be drawn into the corpora cavernosa of the penis P, creating an erection. After the desired rigidity of the penis P is reached, the penis P tensioning device is slid off the vacuum pump device 70 and around the proximal portion of the penis P in order to maintain the erection. Adjustments to the positioning of the penis tensioning device 20 are then made by expanding the medial aperture 21, and moving the device 20, as described above. The length of time the user expands the medial aperture 21, however, is preferably held to a minimum to prevent loss of blood drawn into the corpora cavernosa as a result of the vacuum operation.

Figure 13:
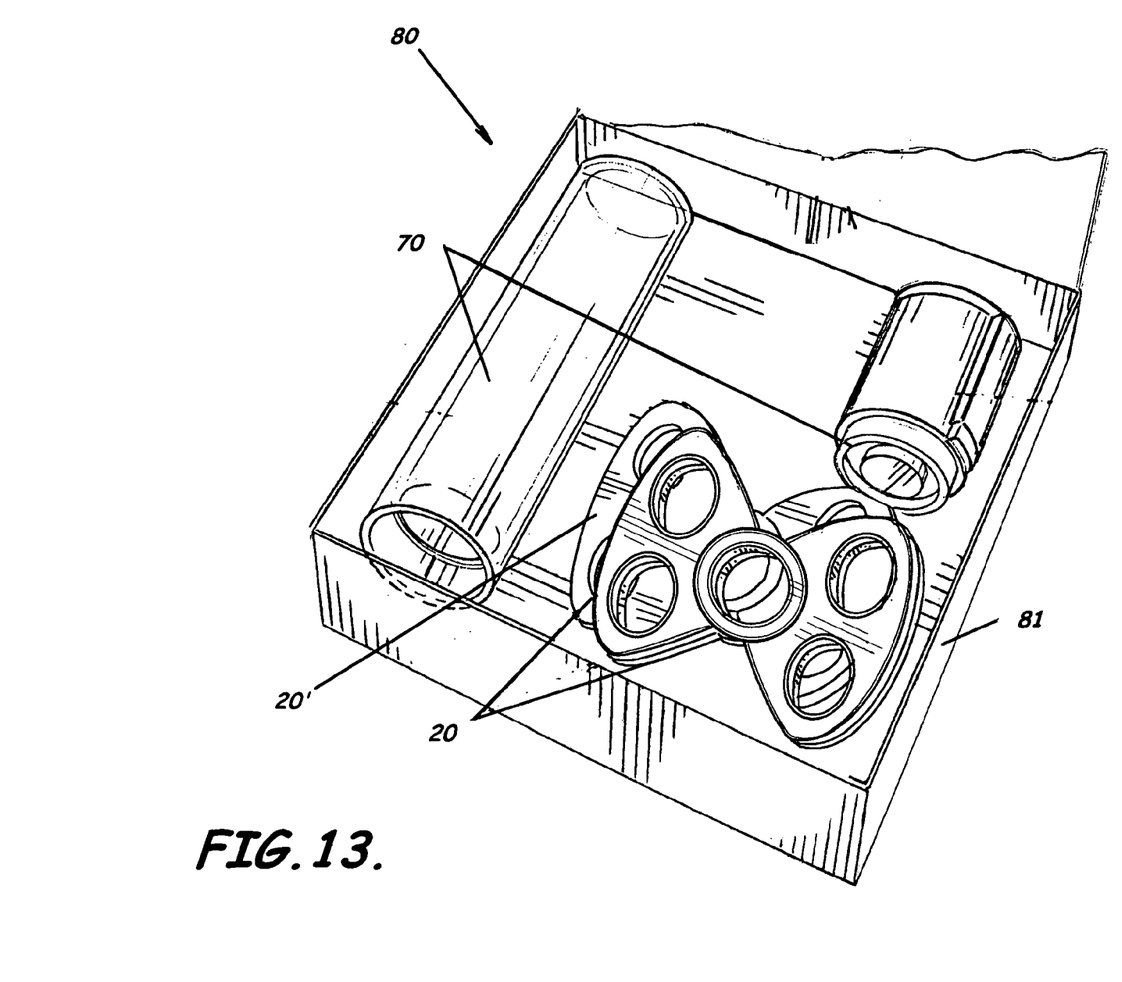
FIG. 13 is a perspective view of a penile tensioning kit, according to an embodiment of the present invention.

As shown in FIG. 13, advantageously an embodiment of the present invention also includes a kit 80 for forming and maintaining an erect penis P. The kit 80 preferably includes a container 81, at least one penile tensioning device 20, described above, positioned in the container 81, and a vacuum device 70, described above, also positioned in the container 81. As perhaps best illustratively shown in FIGS. 4–6, the penile tensioning device 20, various embodiments of which were described in detail above, as a minimum includes a body region of bendable and stretchable material formed in a closed band shape defining a constriction body region 24 having outer constriction body peripheries 26 and inner constriction body peripheries 28, and a plurality of tension positioning and release grips 25, 27, connected to the outer constriction body peripheries 26 of the constriction body region 24. The inner constriction body peripheries 28 of the constriction body region 24 substantially surround a medial aperture 21. The medial aperture 21 includes a longitudinal axis A, a longitudinal length L, and a preselected inner width or diameter D. The inner constriction body peripheries 28 of the medial aperture 21 are adapted to substantially surround and abuttingly contact outer surface peripheries of a proximal portion of a penis P for substantially evenly applying constriction pressure around the circumference of a penis P when so positioned thereon. The tension positioning and release grips 25, 27, are formed of a bendable material connected to the outer peripheries of the constriction body region 24. Each of the tension positioning and release grips 25, 27, have a pair of finger apertures 23 adapted to receive a corresponding plurality of fingers F of the user.

As shown in FIG. 3, the vacuum device 70 includes an elongated vacuum chamber 71 and a pressure pump 72. The elongated vacuum chamber 71 has a proximal end and a distal end. The proximal end is adapted to receive the penile tensioning device 20 thereon and adapted to receive the penis P therein. The vacuum chamber 71 is also adapted to be brought into contact with a user adjacent the proximal end of the penis P against the body of the user in order to form an erect penis P and to aid in positioning the penile tensioning device 20 in abutting contact with the outer surface peripheries of the proximal portion of the erect penis P. The pressure pump 72 is adapted to be connected to the distal end 75 of the vacuum chamber 71 for creating a vacuum pressure inside the vacuum chamber 71. The distal end of the vacuum chamber 71 is adapted to be positioned in fluid communication with the pressure pump 72 whereby a pressure is created by the pressure pump 72 inside the vacuum chamber 71 and exerted upon the penis P received therein to form the erect penis P.

Advantageously, the kit 80 can also include a practice penile tensioning device 20' similar in size and shape to at least one on the penile tensioning device 20, positioned in the container 81. The practice penile tensioning device 20' can have a constriction region 24 of increased pliability, softness, and elasticity for performing repeated practice penile tensioning and removal while minimizing any risk of skin or vascular problems.

As perhaps best shown in FIGS. 1–2, the present invention also advantageously provides methods of using a penile tensioning device 20. A method of using a penile tensioning device 20 preferably includes providing a penile tensioning device 20 including a closed band of material defining a constriction body region 24 having outer constriction body peripheries 26 and inner constriction body peripheries 28 surrounding a medial aperture 21 adapted to receive a penis P of a user therein. The medial aperture 21 can include a plurality of tensioning ribs 22 connected to and positioned axially and preferably uniformly spaced apart along the inner constriction body peripheries 28 and extend inwardly into the medial aperture 21. The penile tensioning device 20 includes a pair of positioning and removal grips 25, 27, connected to the constriction body region 24 along major lengthwise extents 65, 67, preferably having an arcuate shape and located substantially parallel to an arc of a circumference of the medial aperture 21 adjacent the outer constriction body peripheries 26. Each grip 25, 27, is preferably constructed of a material that is preferably harder than the material used to construct the constriction body region 24, and each preferably has at least a pair of separate and spaced apart finger apertures 23 adapted to receive the fingers F of the user and each connected to a major lengthwise extent 65, 67, of an opposing side of the constriction body region 24.

The method also includes stretching a constriction body region 24 of a penile tension device 20 by a plurality of fingers F of a user positioned in the pair of positioning and release grips 25, 27, associated with the penile tension device 20 so that an opposing force is applied to major lengthwise extents 65, 67, of opposing sides of the constriction body region 24 to thereby expand a medial aperture 21 of the constriction body region 24 sufficiently to position the stretched constriction body region 24 over a distal end of a penis P. The user then positions the stretched constriction body region 24 over a distal end of the penis P of the user and toward a proximal portion of the penis P, releasing the stretch of the constriction body region 24 upon reaching the desired position. The inner constriction body peripheries 28 of the constriction body region 24 should abuttingly contact outer surfaces of the proximal portion of the penis P to provide substantially uniform constriction pressure around the outer penal surface peripheries of the proximal portion of the penis P. The user can, however, make adjustments to the position of the penile tensioning device 20, as desired, by selectively re-stretching the constriction body region 24, repositioning the device 20, and releasing the stretch. Note, as desired, a lubricant, e.g., an oil-based jelly or liquid, a water-based jelly or liquid, or various other lubricants as understood by those skilled in the art, can be positioned on the construction body region 24 prior to the step of positioning the stretched constriction body region 24 over a distal end of the penis P of the user to aid in the positioning and readjusting process. Upon completion of the use of the device 20, the user can again re-stretch the construction body region 24 to release the tension upon the proximal portion of the penis P, reposition the stretched constriction body region 24 from the proximal portion of the penis P over the distal end, and again release the stretch of the constriction body region 24 once clear the distal end of the penis P.

As perhaps best shown in FIGS. 1–3, another method of using a penile tensioning device 20 preferably includes providing a penile tensioning device 20 including a closed band of material defining a constriction body region 24 having outer constriction body peripheries 26 and inner constriction body peripheries 28 surrounding a medial aperture 21 adapted to receive a penis of a user therein, and a pair of tension positioning and removal grips 25, 27, connected to the constriction body region 24 along major lengthwise extents 65, 67, preferably having an arcuate shape and preferably located substantially parallel to an arc of a circumference of the medial aperture 21, each of the grips 25, 27, preferably having a pair of separate and spaced apart finger apertures 23 adapted to receive the fingers F of the user.

The method also includes stretching a constriction body region 24 of the penile tension device 20 by a plurality of fingers F of a user positioned in a pair of positioning and release grips 25, 27, associated with the penile tension device 20 so that an opposing force is applied to the major lengthwise extents 65, 67, of opposing sides of the constriction body region 24 to thereby expand a medial aperture 21 of the constriction body region 24 sufficiently to position the stretched constriction body region 24 over a proximal end 74 of a vacuum device 70 for placement over a penis P of the user. After positioning for the constriction body region 24 over the proximal end 74 of the vacuum device 70, the user can place the penis P inside an elongated vacuum chamber 71 of the vacuum device 70 from a proximal end thereof, pressing an open portion of the proximal end 74 against the body of the user to ensure an airtight seal and pump air out of the vacuum chamber 71 from a distal end 75 thereof to create a pressure therewithin.

After sufficient rigidity of the penis P is obtained, the user can install the penile tensioning device 20 by sliding or otherwise repositioning the penile tensioning device 20 to a proximal portion of a penis P of the user, thereby releasing the stretch of the constriction body region 24 so that inner constriction body peripheries 28 of the constriction body region 24 abuttingly contact outer surfaces of the proximal portion of the penis P. The user can make adjustments to the position of the penile tensioning device 20, as desired, by selectively re-stretching the constriction body region 24, repositioning the device 20, and releasing the stretch. Note, a lubricant, e.g., an oil-based jelly or liquid, a water-based jelly or liquid, or various other lubricants as understood by those skilled in the art, can be positioned on the inner peripheries of the constriction region 24 or the proximal end of the vacuum chamber 71 prior to either the step of positioning the stretched constriction body region 24 over the proximal end of the vacuum chamber 71 or the step of positioning the stretched constriction body region 24 over a proximal end of the penis P of the user.

Upon completion of the use of the device 20, the user can remove the penile tensioning device from the erect penis by again stretching the constriction body region 24 to release the tension upon the proximal portion of the penis P, repositioning the stretched constriction body region 24 from the proximal portion of the penis P over the distal end, and again releasing the stretch of the constriction body region 24. Advantageously, the penis P can be either erect or flaccid prior to removal.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification. For example, the medial aperture was depicted as circular but may be shaped in any manner consistent with conforming around the outer peripheries of the proximal end of the penis. Also for example, though that tension positioning and removal grips were described with respect to a pair, additional grips connected to the constriction body region are within the scope of the present invention. Also for example, the system and the kit were described with respect to the embodiment shown in FIGS. 4–5 for illustrative purposes only. Other configurations including those described in FIGS. 6–12 are, of course, within the scope of the present invention.

What is claimed is:

1. A penile tensioning device comprising:
    a body region of bendable and stretchable material formed in a closed band shape defining a constriction body region and including outer constriction body peripheries and inner constriction body peripheries, the inner construction body peripheries adapted to substantially surround and abuttingly contact outer penile surface peripheries of a proximal portion of a penis of a user for substantially evenly applying constriction pressure around the circumference of the penis when positioned thereon and substantially surrounding a medial aperture having a longitudinal medial aperture axis, a preselected longitudinal medial aperture length, and a preselected inner medial aperture diameter;
    a pair of tension positioning and release grips formed of a bendable material and connected to the outer constriction body peripheries of the constriction body region, each pair of tension positioning and release grips also having a pair of separate and spaced apart finger apertures adapted to receive a corresponding pair of fingers of the user, a first of the pair of tension positioning and release grips positioned substantially opposite a second of the pair of tension positioning and release grips on the outer constriction body peripheries for the user to impart a first radial outwardly directed stretching force to the constriction body region to increase the preselected inner medial aperture diameter to allow positioning of the penile tensioning device in abutting contact with the outer penile surface peripheries of the proximal portion of the penis to thereby allow constriction of bloodflow to the penis and for the user to impart a second radial outwardly directed stretching force to the outer constriction body peripheries to increase the preselected inner medial aperture diameter to allow removal of the penile tensioning device from such abutting contact with the outer penile surface peripheries of the proximal portion of the penis to thereby allow passage of the penile tensioning device over a glands penis; and
    a plurality of tensioning ribs connected to and positioned uniformly and axially spaced apart along the inner constriction body peripheries of the constriction body region, extending inwardly into the medial aperture, extending substantially parallel to the longitudinal medial aperture axis, and extending substantially the longitudinal medial aperture length to thereby provide substantially uniform constriction pressure around the outer penile surface peripheries of the proximal portion of the penis when positioned thereon.

2. A device of claim 1, wherein the medial aperture has a proximal medial aperture end and a distal medial aperture end, and wherein the inner constriction body peripheries are arcuate along the longitudinal medial aperture length extending between the proximal medial aperture end and the distal medial aperture end to provide greater tensioning at a midpoint of the longitudinal medial aperture length tan at the proximal medial aperture end and the distal medial aperture end.

3. A device of claim 1, wherein the medial aperture includes a horizontal axis and a vertical axis, and wherein a shape of the portion of the positioning and release grips adjacent the medial aperture is such that application of the second radial outwardly directed stretching force to the outer constriction body peripheries to increase the preselected inner medial aperture diameter causes application of force such that the preselected inner medial aperture diameter expands along lie horizontal axis without decreasing along the vertical axis.

4. A device of claim 1, wherein the outer constriction body peripheries of the constriction body region further includes a pair of major lengthwise extents having an arcuate shape positioned on opposing sides of the constriction body region and positioned substantially parallel to an arc of a circumference of the medial aperture, and wherein each of the tensioning and release grips is connected to one of the pair of major lengthwise extents to thereby expand the medial aperture of the constriction body region so that the stretching of the constriction body region is substantially uniform along at least the major lengthwise extent.

5. A device of claim 1, wherein the constriction body region has a proximal side and a distal side, each side comprising substantially half of the constriction body region, and wherein the proximal and distal sides are laminated together to form the constriction body region.

6. A device of claim 1, wherein the constriction body region is unitary and wherein a proximal side and a distal side of the pair of tensioning and removal grips are laminated together and Her laminated to the outer constriction body peripheries.

7. A device of claim 1, wherein the positioning and release grips include outer grip peripheries, wherein the outer constriction body surface peripheries have a longitudinal length, wherein a portion of the positioning and release grips adjacent the medial aperture has a longitudinal length substantially similar to the longitudinal length of the outer constriction body surface peripheries, and wherein the longitudinal length of the positioning and release grips progressively decreases between the outer constriction body peripheries and the outer grip peripheries.

8. A device of claim 1, wherein a first material forming the constriction body region is softer than a second material forming the positioning and release grips such that application of the first radial outwardly directed stretching force substantially increases the preselected inner medial aperture diameter of the medial aperture and only minimally deforms the finger apertures of the positioning and release grips.

9. A device of claim 1, wherein a predefined portion of material of the constriction body region is adapted to be positioned adjacent the urethra during positioning of the penile tensioning device in abutting contact with the outer penile surface peripheries of the proximal portion of the penis, and wherein the predefined portion of material is softer than other portions of the material of the constriction body region to thereby provide reduced constriction on the urethra.

10. A penile tensioning device for forming and maintaining an erect penis comprising:
a body region of bendable and stretchable material formed in a closed band shape defining a constriction body region and including outer constriction body peripheries and inner constriction body peripheries, the inner construction body peripheries adapted to substantially surround and abuttingly contact outer penile surface peripheries of a proximal portion of a penis of a user for substantially evenly applying constriction pressure around the circumference of the penis when positioned thereon and substantially surrounding a medial aperture having a longitudinal medial aperture axis, a longitudinal medial aperture length, and a preselected inner medial aperture diameter; and
a plurality of tension positioning and release grips comprising a bendable material and connected to the outer constriction body peripheries of the constriction body region, each of the plurality of tension positioning and release grips also having a pair of separate and spaced apart finger apertures adapted to receive a corresponding pair of fingers of the user, a first of the plurality of tension positioning and release grips positioned along substantially the entire length of a major lengthwise extent substantially opposite a second of the plurality of tension positioning and release grips also positioned along substantially the entire length of another major lengthwise extent and each connected to the outer constriction body peripheries for the user to impart a radial outwardly directed stretching force to the constriction body region along each of the major lengthwise extents to increase the predetermined inner medial aperture diameter and thereby allowing removal of the penile tensioning device from abutting contact with the outer surface peripheries of the proximal portion of the penis and allowing passage of the penile tensioning device over a glands penis.

11. A device of claim 10, wherein the radial outwardly directed stretching force is a first radial outwardly directed stretching force, and wherein the plurality of tension positioning and release grips also provide a second radial outwardly directed stretching force to the constriction body region to increase the preselected inner medial aperture diameter to allow positioning of the penile tensioning device in abutting contact with the outer surface peripheries of the proximal portion of the penis to thereby allow constriction of bloodflow to the penis.

12. A device of claim 10, further comprising a plurality of tensioning ribs connected to and positioned uniformly and axially spaced apart along the inner constriction body peripheries of the constriction body region, extending inwardly into the medial aperture, extending parallel to the longitudinal medial aperture axis, and extending substantially the longitudinal medial aperture length, to provide substantially uniform constriction pressure around the outer peripheries of the proximal portion of the penis when positioned thereon.

13. A device of claim 10, wherein the medial aperture has a proximal medial aperture end and a distal medial aperture end, and wherein the inner constriction body peripheries are arcuate along the longitudinal medial aperture length extending between the proximal medial aperture end and the distal medial aperture end to provide greater tensioning at a midpoint of the longitudinal medial aperture length an at the proximal medial aperture end and the distal medial aperture end.

14. A device of claim 10, wherein the medial aperture includes a horizontal axis and a vertical axis, and wherein a shape of the portion of the positioning and release grips adjacent the medial aperture is such that application of the radial outwardly directed stretching force to the outer constriction body peripheries to increase the preselected inner medial aperture diameter causes application of force such that the preselected inner medial aperture diameter expands along the horizontal axis without decreasing along the vertical axis.

15. A device of claim 10, wherein the outer constriction body peripheries of the constriction body region further includes a pair of major lengthwise extents having an arcuate shape positioned on opposing sides of the constriction body region and positioned substantially parallel to an arc of a circumference of the medial aperture, and wherein each of the tensioning and release grips is connected to one of the pair of major lengthwise extents to thereby expand the medial aperture of the constriction body region so that the stretching of the constriction body region is substantially uniform along at least the major lengthwise extent.

16. A device of claim 10, wherein the constriction body region has a proximal side and a distal side, each side comprising substantially half of the constriction body region, and wherein the proximal and distal sides are laminated together to form the constriction body region.

17. A device of claim 10, wherein the constriction body region is unitary and wherein a proximal side and a distal side of the plurality of tensioning and removal grips are laminated together and further laminated to the outer constriction body peripheries.

18. A device of claim 10, wherein the positioning and release grips include outer grip peripheries, wherein the outer constriction body surface peripheries have a preselected longitudinal length, wherein a portion of the positioning and release grips adjacent the medial aperture has a longitudinal length substantially similar to the longitudinal length of the outer constriction body surface peripheries, and wherein the longitudinal length of the positioning and release grips progressively decreases between the outer constriction body surface peripheries and the outer grip peripheries.

19. A device of claim 10, wherein a first material forming the constriction body region is softer than a second material forming the positioning and release grips such that application of the first radial outwardly directed stretching force substantially increases the preselected inner medial aperture diameter of the medial aperture and only minimally deforms the finger apertures of the positioning and release grips.

20. A device of claim 10, wherein a predefined portion of material of the constriction body region is adapted to be positioned adjacent the urethra during positioning of the penile tensioning device in abutting contact with the outer penile surface peripheries of the proximal portion of the penis, and wherein the predefined portion of material is softer than other portions of the material of the constriction body region to thereby provide reduced constriction on the urethra.

21. A penile tensioning system comprising:
a penile tensioning device including:
a body region of bendable and stretchable material formed in a closed band shape defining a constriction body region and including outer constriction body peripheries and inner constriction body peripheries, the inner construction body peripheries adapted to substantially surround and abuttingly contact outer penile surface peripheries of a proximal portion of a penis of a user for substantially evenly applying constriction pressure around the circumference of the penis when positioned thereon and substantially surrounding a medial aperture, the medial aperture having a longitudinal medial aperture axis, a preselected longitudinal medial aperture length, and a preselected inner medial aperture diameter; and
a plurality of tension positioning and release grips comprising a bendable material and connected to the outer constriction body peripheries of the constriction body region, each of the plurality of tension positioning and release grips also having a pair of separate and spaced apart finger apertures adapted to receive a corresponding pair of fingers of a user, a first of the plurality of tension positioning and release grips positioned along substantially the entire length of a major lengthwise extent substantially opposite a second of the plurality of tension positioning and release grips also positioned along substantially the entire length of another major lengthwise extent and each connected to the outer constriction body peripheries for the user to impart a radial outwardly directed stretching force to the constriction body region along each of the major lengthwise extents to increase the predetermined inner medial aperture diameter and thereby allowing removal of the penile tensioning device from abutting contact with the outer surface peripheries of the proximal portion of the penis and allowing passage of the penile tensioning device over a glands penis; and
a vacuum device including:
an elongated vacuum chamber having a proximal vacuum chamber end and a distal vacuum chamber end, the proximal vacuum chamber end adapted to receive the penile tensioning device thereon and adapted to receive the penis therein, the vacuum chamber adapted to be brought into contact with a user adjacent the proximal end of the penis against a body of the user to position the penile tensioning device in abutting contact with the outer penile surface peripheries of the proximal portion of the penis, and
a pressure pump adapted to be connected to the distal vacuum chamber end for creating a vacuum pressure inside the vacuum chamber, the distal vacuum chamber end adapted to be positioned in fluid communication with the pressure pump whereby the vacuum pressure is created by the pressure pump inside the vacuum chamber and exerted upon the penis received therein to form an erect penis.

22. A device of claim 21, wherein the radial outwardly directed stretching force is a first radial outwardly directed stretching force, and wherein the plurality of tension positioning and release grips also provide a second radial outwardly directed stretching force to the constriction body region to increase the preselected inner medial aperture diameter to allow positioning of the penile tensioning device in abutting contact with the outer surface peripheries of the proximal portion of the penis to thereby allow constriction of bloodflow to the penis.

23. A device of claim 21, further comprising a plurality of tensioning ribs connected to and positioned uniformly and axially spaced apart along the inner constriction body peripheries of the constriction body region, extending inwardly into the medial aperture, extending parallel to the longitudinal medial aperture length axis, and extending substantially the preselected longitudinal medial aperture length, to provide substantially uniform constriction pressure around the outer peripheries of the proximal portion of the penis when positioned thereon.

24. A device of claim 21, wherein the medial aperture has a proximal medial aperture end and a distal medial aperture end, and wherein the inner constriction body peripheries are arcuate along the longitudinal medial aperture length extending between the proximal medial aperture end and the distal medial aperture end to provide greater tensioning at a midpoint of the longitudinal medial aperture length than at the proximal medial aperture end and the distal medial aperture end.

25. A device of claim 21, wherein the medial aperture includes a horizontal axis and a vertical axis, and wherein a shape of the portion of the positioning and release grips adjacent the medial aperture is such that application of the radial outwardly directed stretching force to the outer constriction body peripheries to increase the preselected inner medial aperture diameter causes application of force such that the preselected inner medial aperture diameter expands along the horizontal axis without decreasing along the vertical axis.

26. A device of claim 21, wherein the outer constriction body peripheries of the constriction body region further includes a pair of major lengthwise extents having an arcuate shape positioned on opposing sides of the constriction body region and positioned substantially parallel to an arc of a circumference of the medial aperture, and wherein each of the tensioning and release grips is connected to one of the pair of major lengthwise extents to thereby expand the medial aperture of the constriction body region so that the stretching of the constriction body region is substantially uniform along at least the major lengthwise extent.

27. A device of claim 21, wherein the positioning and release grips include outer grip peripheries, wherein the outer constriction body surface peripheries have a preselected longitudinal length, wherein a portion of the positioning and release grips adjacent the medial aperture has a longitudinal length substantially similar to the longitudinal length of the outer constriction body surface peripheries, and wherein the longitudinal length of the positioning and release grips progressively decreases between the outer constriction body surface peripheries and the outer grip peripheries.

28. A device of claim 21, wherein a first material forming the constriction body region is softer than a second material forming the positioning and release grips such that application of the first radial outwardly directed stretching force substantially increases the preselected inner medial aperture diameter of the medial aperture and only minimally deforms the finger apertures of the positioning and release grips.

29. A device of claim 21, wherein a predefined portion of material of the constriction body region is adapted to be positioned adjacent the urethra during positioning of the penile tensioning device in abutting contact with the outer penile surface peripheries of the proximal portion of the penis, and wherein the predefined portion of material is softer than other portions of the material of the constriction body region to thereby provide reduced constriction on the urethra.

30. A penile tensioning kit comprising:
a container;
a penile tensioning device positioned within the container and including:
a body region of bendable and stretchable material formed in a closed band shape defining a constriction body region and including outer constriction body peripheries and inner constriction body peripheries, the inner construction body peripheries adapted to substantially surround and abuttingly contact outer penile surface peripheries of a proximal portion of a penis of a user for substantially evenly applying constriction pressure around the circumference of the penis when positioned thereon and substantially surrounding a medial aperture having a longitudinal medial aperture axis, a longitudinal medial aperture length, and a preselected inner medial aperture diameter; and
a pair of tension positioning and release grips composed of a bendable material and connected to the outer constriction body peripheries of the constriction body region, each of the pair of tension positioning and release grips also having a pair of separate and spaced apart finger apertures adapted to receive a corresponding pair of fingers of the user, a first of the pair of tension positioning and release grips positioned substantially opposite a second of the pair of tension positioning and release grips on the outer constriction body peripheries for the user to impart a radial outwardly directed stretching force to the constriction body region to increase the predetermined inner medial aperture diameter to allow removal of the penile tensioning device from abutting contact with the outer surface peripheries of the proximal portion of the penis to allow passage of the penile tensioning device over a glands penis; and
a practice penile tensioning device positioned in the container having a constriction body region of increased elasticity and softness and otherwise substantially similar to the penile tensioning device for performing practice penile tensioning and removal.

31. A penile tensioning kit of claim 30, further comprising:
a vacuum device positioned in the container and including:
an elongated vacuum chamber having a proximal end and a distal end, the proximal end adapted to receive the penile tensioning device thereon and adapted to receive the penis therein, the vacuum chamber adapted to be brought into contact with the user adjacent the proximal end of the penis against a body of the user to position the penile tensioning device in abutting contact with the outer surface peripheries of the proximal portion of the erect penis, and
a pressure pump adapted to be connected to the distal end of the vacuum chamber for creating a vacuum pressure inside the vacuum chamber, the distal end of the vacuum chamber adapted to be positioned in fluid communication with the pressure pump whereby a pressure is created by the pressure pump inside the vacuum chamber and exerted upon the penis received therein to form the erect penis.

32. A kit of claim 30, further comprising a plurality of tensioning ribs connected to and positioned uniformly and axially spaced apart along the inner constriction body peripheries of the constriction body region, extending inwardly into the medial aperture, extending parallel to the longitudinal medial aperture length axis, and extending substantially the preselected longitudinal medial aperture length, to provide substantially uniform constriction pressure around the outer peripheries of the proximal portion of the erect penis when positioned thereon.

33. A kit of claim 30, wherein the medial aperture of the penile tensioning device has a proximal medial aperture end and a distal medial aperture end, and wherein the inner constriction body peripheries are arcuate along the longitudinal medial aperture length extending between the proximal medial aperture end and the distal medial aperture end to provide greater tensioning at a midpoint of the longitudinal medial aperture length than at the proximal medial aperture end and the distal medial aperture end.

34. A kit of claim 30, wherein the positioning and release grips include outer grip peripheries, wherein the outer constriction body surface peripheries have a preselected longitudinal length, wherein a portion of the positioning and release grips adjacent the medial aperture has a longitudinal length substantially similar to the longitudinal length of the outer constriction body surface peripheries, and wherein the longitudinal length of the positioning and release grips progressively decreases between the outer constriction body surface peripheries and the outer grip peripheries.

35. A kit of claim 30, wherein a first material forming the constriction body region of the penile tensioning device is softer than a second material forming the positioning and release grips such that application of the first radial outwardly directed stretching force substantially increases the preselected inner medial aperture diameter of the medial aperture and only minimally deforms the finger apertures of the positioning and release grips.

36. A kit of claim 30, wherein a predefined portion of material of the constriction body region of the penile tensioning device is adapted to be positioned adjacent the urethra during positioning of the penile tensioning device in abutting contact with the outer penile surface peripheries of the proximal portion of the penis, and wherein the predefined portion of material is softer than other portions of the material of the constriction body region to thereby provide reduced constriction on the urethra.

37. A method of using a penile tensioning device, the method comprising the step of:
stretching a constriction body region of a penile tension device by a plurality of fingers of a user positioned in a pair of separate and spaced apart positioning and release grips associated with the penile tension device and each connected to substantially the entire length of a major lengthwise extent of an opposing side of the constriction body region so that an opposing force is applied to and along each of the respective major lengthwise extents of the opposing sides of the constriction body region to thereby expand a medial aperture of the constriction body region sufficiently to position the stretched constriction body region over a distal end of a penis of the user and toward a proximal portion of the penis.

38. A method of claim 37, wherein the step of stretching includes positioning the plurality of fingers of a user in at least two separate and spaced-apart finger apertures formed in each of the pair positioning and release grips.

39. A method of claim 37, wherein the plurality of fingers of the user includes a pair of fingers of each hand of the user.

40. A method of claim 37, wherein the step of stretching includes each of the major lengthwise extents having an arcuate shape substantially parallel to an arc of a circumference of the medial aperture.

41. A method of claim 37, wherein the constriction body region is formed of a softer material than the positioning and release grips so that the stretching of the constriction body region is substantially uniform along at least the major lengthwise extent.

42. A method of using a penile tensioning device, the method comprising the steps of:

stretching a constriction body region formed of a relatively soft material of a penile tension device by a plurality of fingers of a user positioned in a pair of positioning and release grips formed of a relatively harder material than the constriction body region and associated with the penile tension device so that an opposing force is applied in a substantially uniform manner to and along the major lengthwise extents of the opposing sides of the soft material of the constriction body region to thereby expand a medial aperture of the constriction body region sufficiently to position the stretched constriction body region over a proximal end of a vacuum device for placement over a penis of the user; and repositioning the device off the proximal end of the vacuum device and onto a proximal portion of the penis of the user, thereby releasing the stretch of the constriction body region so that inner constriction body peripheries of the constriction body region abuttingly contact with and provide substantially uniform constriction pressure around outer penile surface peripheries of the proximal portion of the penis.

\* \* \* \* \*